United States Patent [19]

Norman et al.

[11] Patent Number: 6,096,913
[45] Date of Patent: Aug. 1, 2000

[54] PRODUCTION OF METAL-LIGAND COMPLEXES

[75] Inventors: John Anthony Thomas Norman, Encinitas; Yoshihide Senzaki, Carlsbad; David Allen Roberts, Escondido, all of Calif.

[73] Assignee: Air Products and Chemicals, Inc., Allentown, Pa.

[21] Appl. No.: 09/329,417

[22] Filed: Jun. 10, 1999

[51] Int. Cl.[7] .............................. C07F 1/08; C23C 16/00
[52] U.S. Cl. .............................. 556/12; 556/21; 556/113; 556/117; 427/248.1
[58] Field of Search .................... 556/113, 117, 556/12, 21; 427/248.1

[56] References Cited

U.S. PATENT DOCUMENTS

| | | | |
|---|---|---|---|
| 4,279,874 | 7/1981 | Doyle | 423/246 |
| 4,385,005 | 5/1983 | Doyle | 260/464 |
| 4,425,281 | 1/1984 | Doyle | 260/430 |
| 4,434,317 | 2/1984 | Doyle et al. | 585/845 |
| 4,471,152 | 9/1984 | Doyle et al. | 585/843 |
| 5,663,391 | 9/1997 | Machida et al. | 556/12 |

OTHER PUBLICATIONS

"Alkene and Carbon Monoxide Derivatives of Copper(I) and Silver(I) β–Diketonates", by G. Doyle, et. al., Organometallics, vol. 4, No. 5, 1985, pp. 830–835.

*Primary Examiner*—Porfirio Nazario-Gonzalez
*Attorney, Agent, or Firm*—Geoffrey L. Chase

[57] ABSTRACT

In a process for the synthesis of a first metal-ligand complex, $M^{+n}(L^-)_n$, where $n \geq 1$, from a metal compound precursor and a ligand precursor, where the metal of the metal compound precursor may during the synthesis change to a valence in excess of n; the improvement, to suppress formation of a second metal-ligand complex of the metal with a valence in excess of n, of adding the elemental form of the metal to the synthesis of the first metal-ligand complex.

22 Claims, No Drawings

PRODUCTION OF METAL-LIGAND COMPLEXES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

In the semiconductor industry there is a growing need for metallization processes, particularly copper metallization processes, that can be used to grow high purity metal films, such as copper films, onto silicon wafer surfaces. These copper films then form the basis for creating the microscopic high speed electrical interconnect pathways or 'lines' that are buried inside the architecture of advanced microprocessors. A key technology for fabricating these metal films, such as copper films, is Chemical Vapor Deposition (CVD). In this approach, a metal (i.e., copper) containing chemical vapor is contacted with a heated substrate surface in such a way that a surface chemical reaction occurs to deposit a pure metal (i.e., copper) film. To ensure the purity of the metal film, the CVD precursor must itself be of high purity. For example, the leading copper precursors for the CVD of copper films are of the type copper$^{(+1)}$(β-diketonate)(A), where (A) is a neutral ligand usually of the unsaturated type. Within this class of compounds the leading candidate is copper$^{(+1)}$(hexafluoro-2,4-pentanedionate)(trimethylvinylsilane), known commercially as CupraSelect® precursor available from the Schumacher unit of Air Products and Chemicals, Inc., Carlsbad, Calif.

This compound and its synthesis has been described in U.S. Pat. No. 5,144,049 by the synthesis route using CuCl rather than $Cu_2O$ as the metal compound precursor.

The synthesis of other similar metal β-diketonates is described in "Alkene and Carbon Monoxide Derivatives of Copper(I) and Silver(I) β-Diketonates", by G. Doyle, et. al., Organometallics, Vol. 4, No. 5, 1985, pp. 830–835.

Doyle also obtained several patents on the use of copper β-diketonates as adsorbents for various unsaturated materials, i.e., U.S. Pat. No. 4,279,874; U.S. Pat. No. 4,385,005; U.S. Pat. No. 4,425,281; U.S. Pat. No. 4,434,317; and U.S. Pat. No. 4,471,152.

Dehydration of this type of compound after synthesis using the $Cu_2O$ synthesis route is described in U.S. Pat. No. 5,663,391 where anhydrous copper sulfate was added to the synthesis mixture to achieve dehydration of the desired product.

Typically, during the synthesis of this class of compounds, undesired side reactions occur to form undesired side products which must then be removed. Specifically, in the case where the β-diketone is hexafluoro-2,4-pentanedione, an undesired side reaction product that can form is $Cu^{+2}$(hexafluoro-2,4-pentanedionate)$_2$. This dark blue colored solid copper complex dissolves into the desired copper$^{(+1)}$(β-diketonate)(A) product, and since the latter species are typically bright yellow, the resulting solution is green. High concentrations of the $Cu^{+2}$(hexafluoro-2,4-pentanedionate)$_2$ by-product lead to inefficiencies in subsequent purification processes resulting in lowered yields of the desired copper$^{(+1)}$(hexafluoro-2,4-pentanedionate)(A) precursor.

The present invention describes how the synthesis of these metal-ligand complexes, such as copper$^{(+1)}$(hexafluoro-2,4-pentanedionate)(A), can be carried out in such a way that the formation of the undesired higher valence metal-ligand complexes, such as $Cu^{+2}$(hexafluoro-2,4-pentanedionate)$_2$, is suppressed. The resulting lowered concentration of higher valence metal-ligand complexes (i.e., $Cu^{+2}$(hexafluoro-2,4-pentanedionate)$_2$) in the crude reaction product thus facilitates more efficient purification steps and consequently a higher yield of pure product.

BRIEF SUMMARY OF THE INVENTION

The present invention is a process for the synthesis of a first metal-ligand complex, $M^{+n}(L^-)_n$, where $n \geq 1$, from a metal compound precursor and a ligand precursor, where the metal of the metal compound precursor is capable of changing to a valence in excess of n during the synthesis; the improvement, to suppress formation of a second metal-ligand complex of the metal with a valence in excess of n, of adding an elemental form of a metal to the synthesis of the first metal-ligand complex.

Preferably, the metal is a transition metal.

More preferably, the metal is copper.

Preferably, the elemental form of the metal is a particulate form.

More preferably, the particulate form has an average particle size of less than 100 mm.

More preferably, the particle size is in the range of 0.01 microns to 100 mm.

Preferably, the ligand precursor is selected from the group consisting of β-diketones, halogenated β-diketones, β-ketoimines, halogenated β-ketoimines, β-diimines, halogenated β-diimines, β-ketoesters, halogenated β-ketoesters, carboxylic acids, halogenated carboxylic acids, phenols, halogenated phenols, amides, halogenated amides, alcohols, halogenated alcohols, amines and mixtures thereof.

More preferably, the ligand precursor is a β-diketone having a formula:

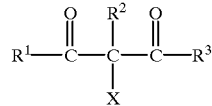

where $R^1$ and $R^3$ are each independently $C_{1-8}$ alkyl, including halogenated alkyl; aryl including halogenated aryl and $R^2$ is H, halogen or $C_{1-8}$ alkyl or halogenated alkyl and X is H.

Most preferably, the ligand precursor is selected from the group consisting of 1,1,1,5,5,5-hexafluoro-2,4-pentanedione, 1,1,1,3,5,5,5-heptafluoro-2,4-pentanedione and mixtures thereof.

Preferably, n is in the range of 1–3.

Preferably, the elemental form of the metal is added in an amount of at least 0.01 weight percent of the metal compound precursor.

More preferably, the present invention is a process for the synthesis of $Cu^{+1}$(1,1,1,5,5,5-hexafluoro-2,4-pentanedionate)$^{-1}$(stabilizing ligand), from the metal compound precursor, cuprous oxide, the ligand precursor, 1,1,1,5,5,5-hexafluoro-2,4-pentanedione and a stabilizing ligand, the improvement, to suppress the formation of $Cu^{+2}$(1,1,1,5,5,5-hexafluoro-2,4-pentanedione)$_2$, of adding elemental particulate copper to the synthesis of the $Cu^{+1}$(1,1,5,5,5-hexafluoro-2,4-pentanedionate)$^{-1}$(stabilizing ligand).

Preferably, the stabilizing ligand is selected from the group consisting of trimethylvinylsilane, alkenes, dienes, silicon substituted alkenes, silicon substituted dienes, alkynes, silicon substituted alkynes, alkyne-alkenes, silicon substituted alkynes-alkenes, nitrites, silicon substituted nitrites, isonitriles, silicon substituted isonitriles, carbon monoxide, trialkyl phosphines, triaryl phosphines, imines, diimines, amines and mixtures thereof.

Most preferably, the stabilizing ligand has a formula: $C(R^4)(R^5)=C(R^5)Si(R^6)_3$, where $R^4$ is H, $C_{1-8}$ alkyl or $Si(R^6)_3$, each $R^5$ is independently H or $C_{1-8}$ alkyl, and each $R^6$ is independently phenyl or $C_{1-8}$ alkyl.

In a most preferred embodiment, the present invention is a process for the synthesis of $Cu^{+1}(1,1,1,5,5,5$-hexafluoro-2,4-pentanedionate$)^{-1}$.(trimethylvinylsilane), from the metal precursor, cuprous oxide, the ligand precursor, 1,1,1,5,5,5-hexafluoro-2,4-pentanedione, and trimethylvinylsilane; the improvement, to suppress the formation of $Cu^{+2}(1,1,1,5,5,5$-hexafluoro-2,4-pentanedionate$)_2$, of adding elemental particulate copper to the synthesis of the $Cu^{+1}(1,1,1,5,5,5$-hexafluoro-2,4-pentanedionate$)^{-1}$ (trimethylvinylsilane).

Preferably, the particulate copper has a particle size of less than 100 mm.

More preferably, the particle size is in the range of 0.01 to 100 mm.

Preferably, the free copper is added in an amount of at least 0.01 weight percent of the metal precursor, copper oxide.

More preferably, the free copper is added in an amount in the range of 0.01 to 100 weight percent of the copper oxide precursor.

BRIEF DESCRIPTION OF SEVERAL VIEWS OF THE DRAWINGS

Not Applicable

DETAILED DESCRIPTION OF THE INVENTION

The present invention is a synthesis of metal-ligand complexes, such as copper$^{(+1)}(1,1,1,5,5,5$-hexafluoro-2,4-pentanedionate)(A), so that the formation of undesired higher valence metal-ligand complexes, such as $Cu^{+2}(1,1,1,5,5,5$-hexafluoro-2,4-pentanedionate$)_2$, is suppressed. The resulting lowered concentration of higher valence metal-ligand complexes (i.e., $Cu^{+2}(1,1,15,5,5$-hexafluoro-2,4-pentanedionate$)_2$) in the crude reaction product thus facilitates more efficient purification steps and consequently a higher yield of pure product.

Generally, the present invention is a process for the synthesis of a first metal-ligand complex, $M^{+n}(L^-)_n$, where $n \geq 1$, from a metal compound precursor and a ligand precursor, where the metal of the metal compound precursor may during the synthesis change to a valence in excess of n, in which a free or elemental metal, $M^0$, comparable to the metal of the metal compound is added to the synthesis of the first metal-ligand complex to suppress formation of a second metal-ligand complex of the metal with a valence in excess of n.

A particularly desired embodiment of the present invention is a process for the synthesis of $Cu^{+1}(1,1,1,5,5,5$-hexafluoro-2,4-pentanedionate$)^{-1}$(A), from the metal compound precursor, cuprous oxide, the ligand precursor, 1,1,1,5,5,5-hexafluoro-2,4-pentanedione and a stabilizing ligand (A), such as trimethylvinylsilane, where free or elemental particulate copper is added to the synthesis of the $Cu^{+1}(1,1,1,5,5,5$-hexafluoro-2,4-pentanedionate$)^{-1}$(A) to suppress the formation of $Cu^{+2}(1,1,1,5,5,5$-hexafluoro-2,4-pentanedione$)_2$.

The protonated form of the ligand precursor, "L", may be β-diketones, halogenated β-diketones, β-ketoimines, halogenated β-ketoimines, β-diimines, halogenated β-diimines, β-ketoesters, halogenated β-ketoesters, carboxylic acids, halogenated carboxylic acids, phenols, halogenated phenols, amides, halogenated amides, alcohols, halogenated alcohols, amines and mixtures thereof.

The protonated form of the ligand precursor, "L", may be a β-diketone having a formula:

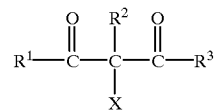

where $R^1$ and $R^3$ are each independently $C_{1-8}$ alkyl, halogenated alkyl, aryl, or halogenated aryl, and $R^2$ is H or halogen, or $C_{1-8}$ alkyl or halogenated alkyl and X is H.

Most preferably, the protonated ligand precursor, "L", is selected from the group consisting of 1,1,1,5,5,5-hexafluoro-2,4-pentanedione, 1,1,1,3,5,5,5-heptafluoro-2,4-pentanedione and mixtures thereof.

The metal-ligand complex may also contain a stabilizing ligand, "A". This would result in a metal-ligand complex of $M^{+n}(L^-)_n$ (A). More preferably, the additional stabilizing ligand "A" is selected from the group consisting of trimethylvinylsilane, alkenes, dienes, silicon substituted alkenes, silicon substituted dienes, alkynes, silicon substituted alkynes, alkyne-alkenes, silicon substituted alkynes-alkenes, nitriles, silicon substituted nitriles, isonitriles, silicon substituted isonitriles, carbon monoxide, trialkyl phosphines, triaryl phosphines, imines, diimines, amines and mixtures thereof. It should be understood that throughout this description, where $M^{+x}(L^-)_x$ or $Cu^{+1}(1,1,1,5,5,5$-hexafluoro-2,4-pentanedionate$)^{-1}$ are recited, that it is contemplated that the metal-ligand complex may include a stabilizing ligand "A".

The metal can broadly meet the following functional definition. If in a chemical reaction to prepare a metal complex of the type $M^{+x}(L^-)_x$ some undesired metal complex species of the type $M^{+(x+y)}(L^-)_{(x+y)}$ forms where (x) can be 1,2,3,4 or 5 and y can be 1,2,3 etc., such that (x+y) cannot exceed 6, then the formation of this undesired species can be suppressed by the addition of a metal N to the reaction which is capable of suppressing the formation of $M^{+(x+y)}(L^-)_{(x+y)}$ by providing the required reducing electrochemical potential. This metal N can be either the same as the metal M or be a different metal chosen such that the desired suppression of $M^{+(x+y)}(L^-)_{(x+y)}$ formation occurs with essentially no deleterious side reactions. Added metal N is also chosen such that if the metal complex $N^{+x}(L^-)_x$ that forms is undesired (formed from the oxidation of N during the suppression of formation of $M^{+(x+y)}(L^-)_{(x+y)}$) then it is readily removed from the reaction mixture. Preferably, the metal is selected from the transition metals. Most preferably it is copper.

The amount of elemental metal powder to be added is an effective amount to achieve at least a detectable suppression of the higher valence metal byproduct, $Cu^{+2}(\beta$-diketonate$)_2$. Preferably, the elemental metal powder would be added in at least a 0.01 weight percent amount in relation to the metal oxide used in the synthesis. More preferably, the elemental metal powder is added in a range of 0.01 to 100 weight percent in relation to the metal oxide. The added elemental or free metal, $M^0$, is typically added as a powder or particulate having a high surface area. The particle size of the metal is no greater than 100 mm, preferably in the range of 0.01 microns to 100 mm. The metal in excess of what is necessary to suppress the metal byproduct may simply be decanted and filtered from the reaction product after synthesis and preferably before further purification steps, such as column chromatography.

The metal precursor compound is typically an oxide or a halide or carboxylate, but other compounds of the metal are acceptable. Preferably, the metal compound is a metal oxide. More preferably, the metal compound is cuprous oxide.

The synthesis of copper$^{(+1)}$($\beta$-diketonate)(A) compounds are achieved via a condensation reaction between copper$^{(+1)}$ oxide and the respective $\beta$-diketone in the presence of a ligand (A) where (A) is typically an olefin, alkyne etc. If the $\beta$-diketone in question is 1,1,1,5,5,5-hexafluoro-2,4-pentanedione, then the reaction occurs according to Equation #1, where 1,1,1,5,5,5-hexafluoro-2,4-pentanedione is abbreviated as "Hhfac", and its corresponding anion, 1,1,1, 5,5,5-hexafluoro-2,4-pentanedionate, as "hfac". This type of synthesis is taught by Doyle, et. al., cited above.

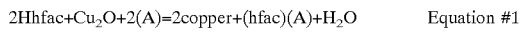

2Hhfac+Cu$_2$O+2(A)=2copper+(hfac)(A)+H$_2$O          Equation #1

However, some Cu$^{+2}$(hfac)$_2$ also forms, which must be removed to allow the isolation of pure copper$^{(+1)}$(hfac)(A). The present invention teaches how the formation of this undesired Cu$^{+2}$(hfac)$_2$ can be suppressed by the addition of finely divided copper powder to the reaction mixture.

The efficacy of this technique was illustrated by conducting a series of syntheses of Cu$^{+1}$(hfac)(trimethylvinylsilane) at both small scale (Experiments #1, #2 and #3) and large scale (Experiments #4, #5 and #6). Experiments #1, #2 and #3 were identical, except that Experiment #3 was conducted with no added copper powder. Experiments #4, #5 and #6 were identical, except that Experiment #6 was conducted with no added copper powder. See the experimental section for details. Once run, the reactions were filtered and their visible light spectrum recorded to directly measure their respective Cu$^{+2}$(hfac)$_2$ concentrations by light absorption at 685 nanometers (nm) and comparing the value obtained to a previously obtained calibration curve of absolute absorbance versus concentration of pure Cu$^{+2}$(hfac)$_2$ in Cu$^{+1}$ (hfac)(trimethylvinylsilane). Trimethylvinylsilane is abbreviated as ("tmvs"). Two different copper powders were used, i.e., either submicron or 10 micron particle size, as shown below. In all cases where copper powder was used, the filtered reaction mixture was noticeably lighter green colored, when compared to the filtered reaction mixture where no copper powder had been added. This is exemplary of successful suppression of Cu$^{+2}$(hfac)$_2$ using the elemental copper powder during the synthesis of Cu$^{+1}$(hfac) (trimethylvinylsilane). The results obtained from the above experiments are shown in Tables 1 and 2, from which it is apparent that the effect of the invention is to successfully suppress undesired metal-ligand complexes of a higher metal valence than desired.

Table 1 reports the experimental runs conducted on the smaller scale.

TABLE 1

| Exp#1 sub-$\mu$m Cu powder | | Exp#2 10 $\mu$m Cu powder | | Exp#3 No Cu powder | |
|---|---|---|---|---|---|
| Abs. Cu$^{+2}$ | 2.50 3710 ppm | Abs. Cu$^{+2}$ | 2.67 4010 ppm | Abs. Cu$^{+2}$ | 5.60 8430 ppm |

The smaller scale experiments were then followed by another three experiments at a larger scale to show that the effect of suppressing the Cu$^{+2}$(hfac)$_2$ concentration is still observed. These experiments were conducted using the 10 micron copper powder. The results are shown below and confirm that the suppression of Cu$^{+2}$(hfac)$_2$ does occur at this higher scale of manufacture, maintaining a lower level of Cu$^{+2}$(hfac)$_2$ by a greater degree than the small scale reaction, probably indicative of superior mixing of reagents at a larger scale.

TABLE 2

| Exp#4 10 micron powder | | Exp#5 10 micron powder | | Exp#6 no copper powder | |
|---|---|---|---|---|---|
| Abs. Cu$^{+2}$ | 0.3 400 ppm | Abs. Cu$^{+2}$ | 0.45 630 ppm | Abs. Cu$^{+2}$ | 1.38 2000 ppm |

Note: In the tables above, to convert the Cu$^{+2}$ concentration into Cu$^{+2}$(hfac)$_2$ concentration, multiply the Cu$^{+2}$concentration by 7.52 which represents the molecular weight of Cu$^{+2}$(hfac)$_2$ divided by the atomic weight of copper (ie 477.6 g/mol/ 63.5 g/mol = 7.52).

Further although it is possible to obtain highly pure product using the metal provision/addition of the present invention without substantive additional purification, using the synthetic procedure and reagent quantities outlined above for Ex.#4 and #5, a series of eight additional experiments were run, and the resulting products were further purified by chromatography. The efficiency of this chromatography step for syntheses conducted using the addition of copper powder was found to be substantially higher than for previous syntheses using no added copper powder. In addition, the chromatography "column life" (how much reaction product could be processed before a fresh column was needed) was found to be almost doubled when using the product low in Cu$^{+2}$(hfac)$_2$ made using the addition of copper powder. These comparisons are shown in the table below.

TABLE 3

Improvements in yield due to copper powder addition.

| Synthesis Technique | No Copper Powder | Addition of Copper Powder | Process Improvement |
|---|---|---|---|
| Column Life | 27 kg | >50 kg | >85% |
| Chromatography Yield | 56% | 82% | 46.4% |

The results recorded in Table 3 show the benefit of the process of the present invention in producing high purity product without reliance on post synthesis purification. As a result, use of the present invention makes the use of various post synthesis purifications optional or at least dependent on the purity level required by a particular enduse. It also allows for the use of less rigorous post synthesis purification, such that chromatographic purification may not be necessary or desired for a given product synthesis.

EXAMPLES 1, 2 & 3

Ex.#1:
Reagents:

| Cu$_2$O | 53 g (0.37 mol). |
| Hhfac | 105 mL (0.74 mol). |
| tmvs | 121 mL (0.784 mol, 6% excess). |
| Copper powder | 1.18 g (0.0185 mol, 5 mol % of Cu$_2$O). particle size: submicron. |

-continued

| Ex.#2: | same reagent values as above for Ex.#1. copper particle size: 10 micron. |
|---|---|
| Ex.#3 (Control): | same reagent values as above for Ex.#1 & #2 above, except no addition of copper powder. |

Procedures for Ex.#1, Ex.#2 and Ex.#3:

Hhfac was added dropwise to a suspension of $Cu_2O/Cu$ (Ex.#1 and #2) or just $Cu_2O$ (Ex.#3) in tmvs at approximately $-10°$ C. for 1.5 hr with stirring. The reaction mixture turned green with remaining red powders. The reaction mixture was stirred at room temperature for 15 hr followed by filtration through 5 g of celite. From the resulting light green liquid product, 5 mL was sampled for spectrophotometric analysis in the visible light region to quantify the concentration of $Cu^{+2}(hfac)_2$ by measuring its visible light absorption at 685 nm.

EXAMPLES 4, 5 & 6

| Ex.#4 and #5: Reagents: | |
|---|---|
| $Cu_2O$ | 5.3 kg. |
| Hhfac | 15.4 kg. |
| tmvs | 7.9 kg. |
| 10 micron copper powder: | 350 g for Ex.#4; 500 g for Ex.#5. |
| Ex.#6 | |
| $Cu_2O$ | 5.1 kg. |
| Hhfac | 14.7 kg. |
| tmvs | 8.1 kg. |
| no addition of copper powder. | |

Procedures for Ex.#4, Ex.#5 and Ex.#6:

Hhfac was added to the copper oxide mixed with copper powder (Ex.#4 and #5) suspended by stirring in a portion of the total tmvs amount and cooled to $-10°$ C. to 0C. Hhfac blended with the remaining tmvs was then pumped into the cooled suspension over approximately 20 hrs, maintaining a temperature of approximately 0C to $-10°$ C. The reaction mixture was then filtered and sampled for $Cu^{+2}(hfac)_2$ content, as for Ex.#1, #2 and #3. The procedure for Ex. #4 and #5 was used for Ex.#6, but no copper powder was added.

As indicated by the experimental results, the present invention provides a remarkable and unexpected enhancement in the synthesis of high purity metal-ligand complexes, such as $Cu^{+1}(hfac)$ (tmvs). The addition of the elemental form of metal powder resulted in dramatic decreases in the by-product $Cu^{+2}(hfac)_2$, well beyond what the inventors expected. The unique synthesis step of the present invention provides higher purity material initially upon synthesis, even without any final purification. This results in significantly increased yields. In addition, the unique synthesis step of the present invention enhances the performance of any subsequent purification processes by decreasing the amount of by-product to be captured. Reduction in load on the subsequent purification process results in extended life for the purification step, such as purification chromatographic columns (i.e., alumina, silica, silica gel, carbons, molecular sieves and porous polymers), previously used to purify the $Cu^{+1}(hfac)$ (tmvs). The overall result is a higher purity, lower cost product using less purification equipment and simplified purification processing.

The present invention has been set forth with regard to several preferred embodiments, but the full scope of the present invention should be ascertained from the claims which follow.

What is claimed is:

1. In a process for the synthesis of a first metal-ligand complex comprising, $M^{+n}(L^-)_n$, where $n \geq 1$, from a metal compound precursor and a ligand precursor, where the metal of said metal compound precursor is capable of changing to a valence in excess of n during the synthesis; the improvement, to suppress formation of a second metal-ligand complex of said metal with a valence in excess of n, of providing an elemental form of a metal for the synthesis of said first metal-ligand complex.

2. The process of claim 1 wherein said metal is a transition metal.

3. In a process for the synthesis of a first metal-ligand complex, $M^{+n}(L^-)_n$, where $n \geq 1$, from a metal compound precursor and a ligand precursor, where the metal of said metal compound precursor is capable of changing to a valence in excess of n during the synthesis; the improvement, to suppress formation of a second metal-ligand complex of said metal with a valence in excess of n, of providing an elemental form of a metal for the synthesis of said first metal-ligand complex wherein said metal compound precursor is a copper compound precursor.

4. The process of claim 1 wherein said elemental form of said metal is a particulate form of said metal.

5. The process of claim 4 wherein said particulate form has a particle size of less than 100 mm.

6. The process of claim 5 wherein said particle size is in the range of 0.01 microns to 100 mm.

7. The process of claim 1 wherein said ligand precursor is selected from the group consisting of β-diketones, halogenated β-diketones, β-ketoimines, halogenated β-ketoimines, β-diimines, halogenated β-diimines, β-ketoesters, halogenated β-ketoesters, carboxylic acids, halogenated carboxylic acids, phenols, halogenated phenols, amides, halogenated amides, alcohols, halogenated alcohols, amines and mixtures thereof.

8. The process of claim 1 wherein said ligand precursor is a β-diketone having a formula:

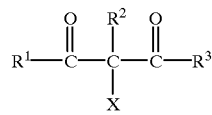

where $R^1$ and $R^3$ are each independently $C_{1-8}$ alkyl or halogenated alkyl, aryl or halogenated aryl, and $R^2$ is H or halogen, or $C_{1-8}$ alkyl or halogenated alkyl and X is H.

9. The process of claim 1 wherein said ligand precursor, is selected from the group consisting of 1,1,1,5,5,5-hexafluoro-2,4-pentanedione, 1,1,1,3,5,5,5-heptafluoro-2,4-pentanedione and mixtures thereof.

10. The process of claim 1 wherein n is in the range of 1–3.

11. The process of claim 1 wherein said elemental form of said metal is added in an amount of at least 0.01 weight percent of the metal compound precursor.

12. The process of claim 1 wherein said $M^{+n}(L^-)_n$ has an additional stabilizing ligand.

13. The process of claim 12 wherein said additional stabilizing ligand is selected from the group consisting of: trimethylvinylsilane, alkenes, dienes, silicon substituted alkenes, silicon substituted dienes, alkynes, silicon substituted alkynes, alkyne-alkenes, silicon substituted alkyne-alkenes, nitrites, silicon substituted nitrites, isonitriles, silicon substituted isonitriles, carbon monoxide, trialkyl phosphines, triaryl phosphines, imines, diimines, amines and mixtures thereof.

14. The process of claim 12 wherein said additional stabilizing ligand has a formula: $C(R^4)(R^5)=C(R^5)Si(R^6)_3$, where $R^4$ is H, $C_{1-8}$ alkyl or $Si(R^6)_3$, each $R^5$ is independently H or $C_{1-8}$ alkyl, and each $R^6$ is independently phenyl or $C_{1-8}$ alkyl.

15. In a process for the synthesis of $Cu^{+1}(1,1,1,5,5,5$-hexafluoro-2,4-pentanedionate$)^{-1}$(stabilizing ligand), from a metal precursor, cuprous oxide, a ligand precursor, 1,1,1,5,5,5-hexafluoro-2,4-pentanedione and a stabilizing ligand; the improvement, to suppress the formation of $Cu^{+2}(1,1,1,5,5,5$-hexafluoro-2,4-pentanedionate$)_2$, of adding elemental particulate copper to the synthesis of said $Cu^{+1}(1,1,1,5,5,5$-hexafluoro-2,4-pentanedionate$)^{-1}$(stabilizing ligand).

16. The process of claim 15 wherein said stabilizing ligand is selected from the group consisting of: trimethylvinylsilane, alkenes, dienes, silicon substituted alkenes, silicon substituted dienes, alkynes, silicon substituted alkynes, alkyne-alkenes, silicon substituted alkyne-alkenes, nitrites, silicon substituted nitrites, isonitriles, silicon substituted isonitriles, carbon monoxide, trialkyl phosphines, triaryl phosphines, imines, diimines, amines and mixtures thereof.

17. The process of claim 15 wherein said stabilizing ligand has a formula: $C(R^4)(R^5)=C(R^5)Si(R^6)_3$, where $R^4$ is H, $C_{1-8}$ alkyl or $Si(R^6)_3$, each $R^5$ is independently H or $C_{1-8}$ alkyl, and each $R^6$ is independently phenyl or $C_{1-8}$ alkyl.

18. In a process for the synthesis of $Cu^{+1}(1,1,1,5,5,5$-hexafluoro-2,4-pentanedionate$)^{-1}$(trimethylvinylsilane), from a metal compound precursor of cuprous oxide, a ligand precursor of 1,1,1,5,5,5-hexafluoro-2,4-pentanedione and trimethylvinylsilane; the improvement, to suppress the formation of $Cu^{+2}(1,1,1,5,5,5$-hexafluoro-2,4-pentanedionate$)_2$, of adding elemental particulate copper to the synthesis of said $Cu^{+1}(1,1,1,5,5,5$-hexafluoro-2,4-pentanedionate$)^{-1}$(trimethylvinylsilane).

19. The process of claim 18 wherein said particulate copper has a particle size of less than 100 mm.

20. The process of claim 19 wherein said particle size is in the range of 0.01 microns to 100 mm.

21. The process of claim 18 wherein said elemental copper is added in an amount of at least 0.01 weight percent of the metal precursor copper oxide.

22. The process of claim 21 wherein said elemental copper is added in an amount in the range of 0.01 to 100 weight percent of the copper oxide precursor.

* * * * *